United States Patent [19]

Sancoff et al.

[11] Patent Number: 5,078,683

[45] Date of Patent: Jan. 7, 1992

[54] PROGRAMMABLE INFUSION SYSTEM

[75] Inventors: Gregory E. Sancoff, Leucadia; Mark McWilliams, San Diego; Howard S. Barr, Escondido; Edward T. Cordner, Jr., Carlsbad; Russell C. Barton, Monrovia, all of Calif.

[73] Assignee: Block Medical, Inc., Carlsbad, Calif.

[21] Appl. No.: 518,987

[22] Filed: May 4, 1990

[51] Int. Cl.$^5$ ............................................. A61M 5/20
[52] U.S. Cl. ........................................ 604/67; 604/31;
                                                       417/474; 128/DIG. 13
[58] Field of Search ................... 604/65, 67, 131, 189,
          604/153, 245, 246, 30, 31; 128/DIG. 12, DIG.
                                              13; 417/44, 45, 474

[56] References Cited

U.S. PATENT DOCUMENTS

| | | | |
|---|---|---|---|
| 4,493,706 | 1/1985 | Borsanyi et al. | |
| 4,551,133 | 11/1985 | Zegers de Beyl et al. | 604/66 |
| 4,553,958 | 11/1985 | LeCocq | 604/67 |
| 4,559,038 | 12/1985 | Berg et al. | |
| 4,559,040 | 12/1985 | Hores et al. | |
| 4,565,542 | 1/1986 | Berg | |
| 4,573,994 | 3/1986 | Fischell et al. | 604/891 |
| 4,650,469 | 3/1987 | Berg et al. | |
| 4,653,987 | 3/1987 | Tsuji et al. | |
| 4,671,792 | 6/1987 | Borsanyi | |
| 4,681,566 | 7/1987 | Fenton, Jr. et al. | 604/135 |
| 4,762,518 | 8/1988 | Kreinick | |
| 4,798,590 | 1/1989 | O'Leary et al. | |
| 4,853,521 | 8/1989 | Claeys et al. | 235/375 |
| 4,925,444 | 5/1990 | Orkin et al. | 604/80 |
| 4,966,579 | 10/1990 | Polaschegg | 604/65 |
| 4,976,590 | 12/1990 | Baldwin | |
| 4,978,335 | 12/1990 | Arthur, III | 604/67 |
| 4,997,347 | 3/1991 | Roos | |

OTHER PUBLICATIONS

Pharmacia Deltec—one page advertisement for the CADD-1, CADD-PCA and CADD-Plus, dated 9/88.
Provider One—sixteen page instruction manual, 2/90.
Provider 6000—sixty-four page operating manual (undated).
Provider 5500—one page advertisement (undated).
Infumed 400—one page advertisement (undated).
Multiplex Series 100 Fluid Management System—three page borchure (1988).
I Flow Multi-Drug Infusion System—four page brochure (undated).

*Primary Examiner*—Stephen C. Pellegrino
*Assistant Examiner*—Steven J. Shumaker
*Attorney, Agent, or Firm*—Baker, Maxham, Jester & Meador

[57] ABSTRACT

A programmable infusion system includes a disposable IV tubing apparatus for conveying intravenous fluid from a source to a patient. A compact, portable case has a receptacle for removably receiving a segment of the disposable apparatus. A peristaltic pump is mounted in the case for engaging the segment of the disposable apparatus and pumping intravenous fluid therethrough. A motor is mounted in the case and is connected for driving the pump upon energization thereof. A bar code reader is mounted in an edge portion of the case for sensing a bar code label attached to the source of intravenous fluid, such as a bag. The bar code label represents the prescribed fluid delivery parameters. These are read and displayed in alphanumeric form by the system when the edge portion of the case containing the bar code reader is passed over the label. A micro-controller mounted in the case energizes the motor so that the peristaltic pump conveys the fluid through the disposable apparatus in accordance with the delivery rate parameters.

8 Claims, 6 Drawing Sheets

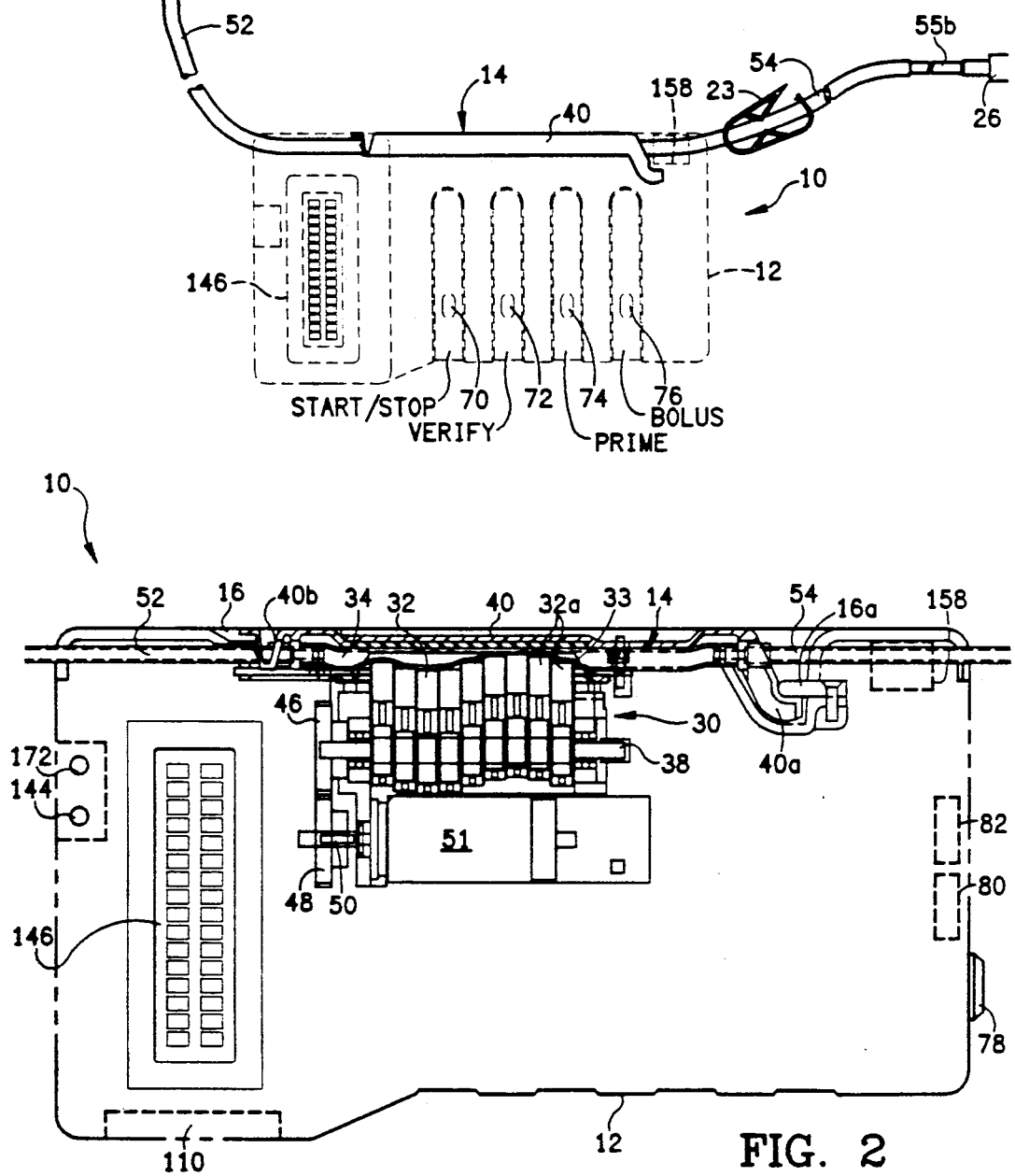

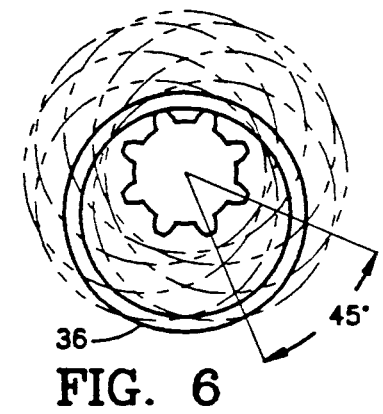
FIG. 6
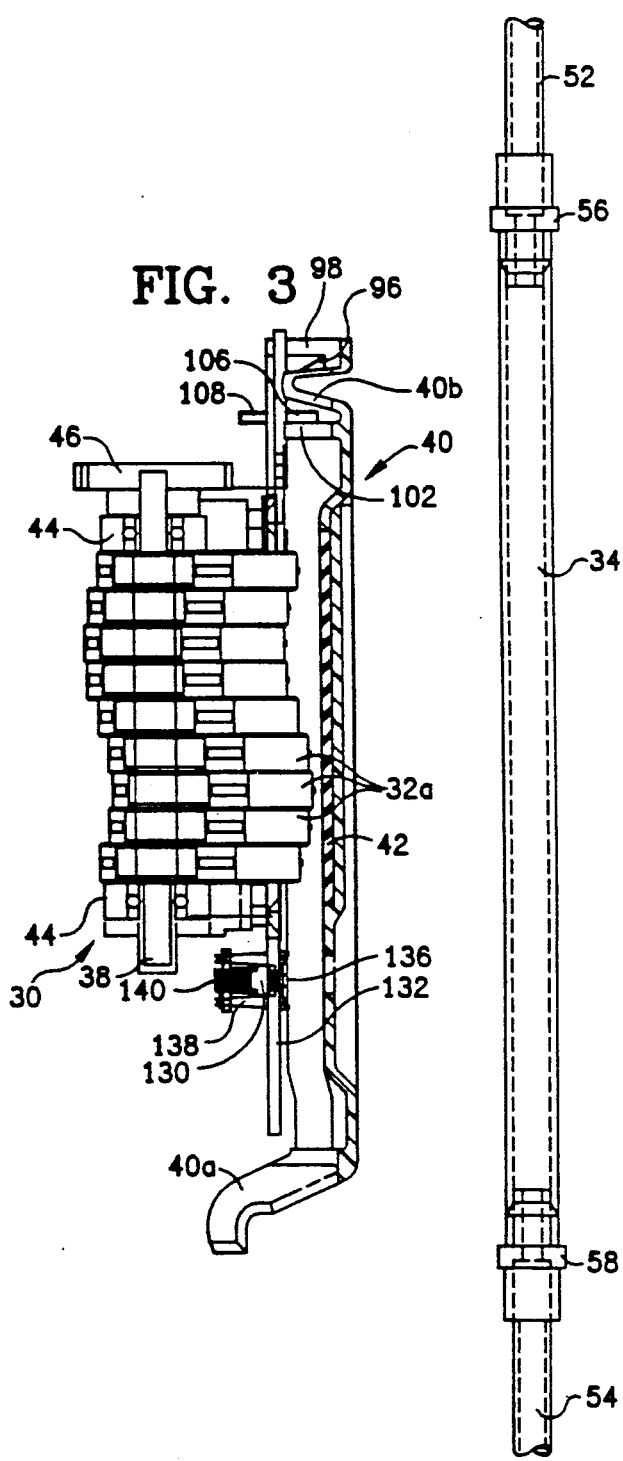
FIG. 3
FIG. 4
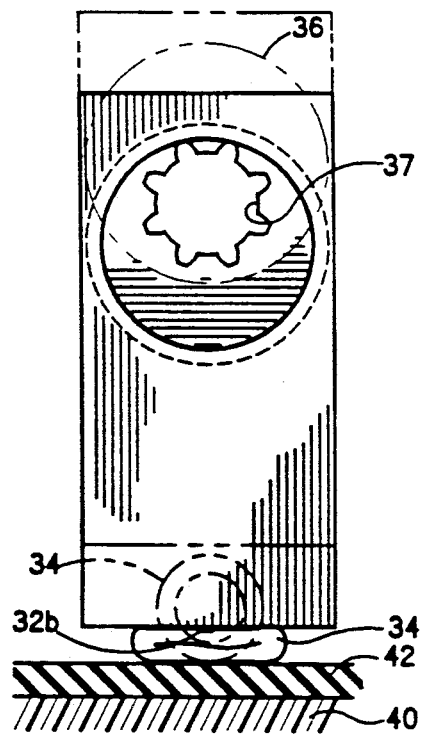
FIG. 5

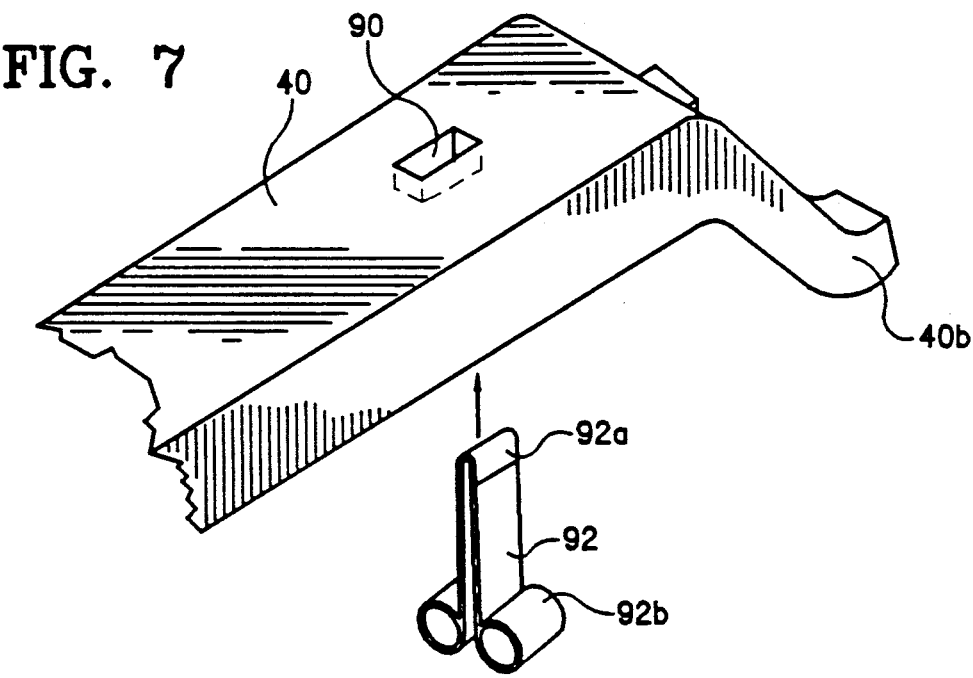
FIG. 7
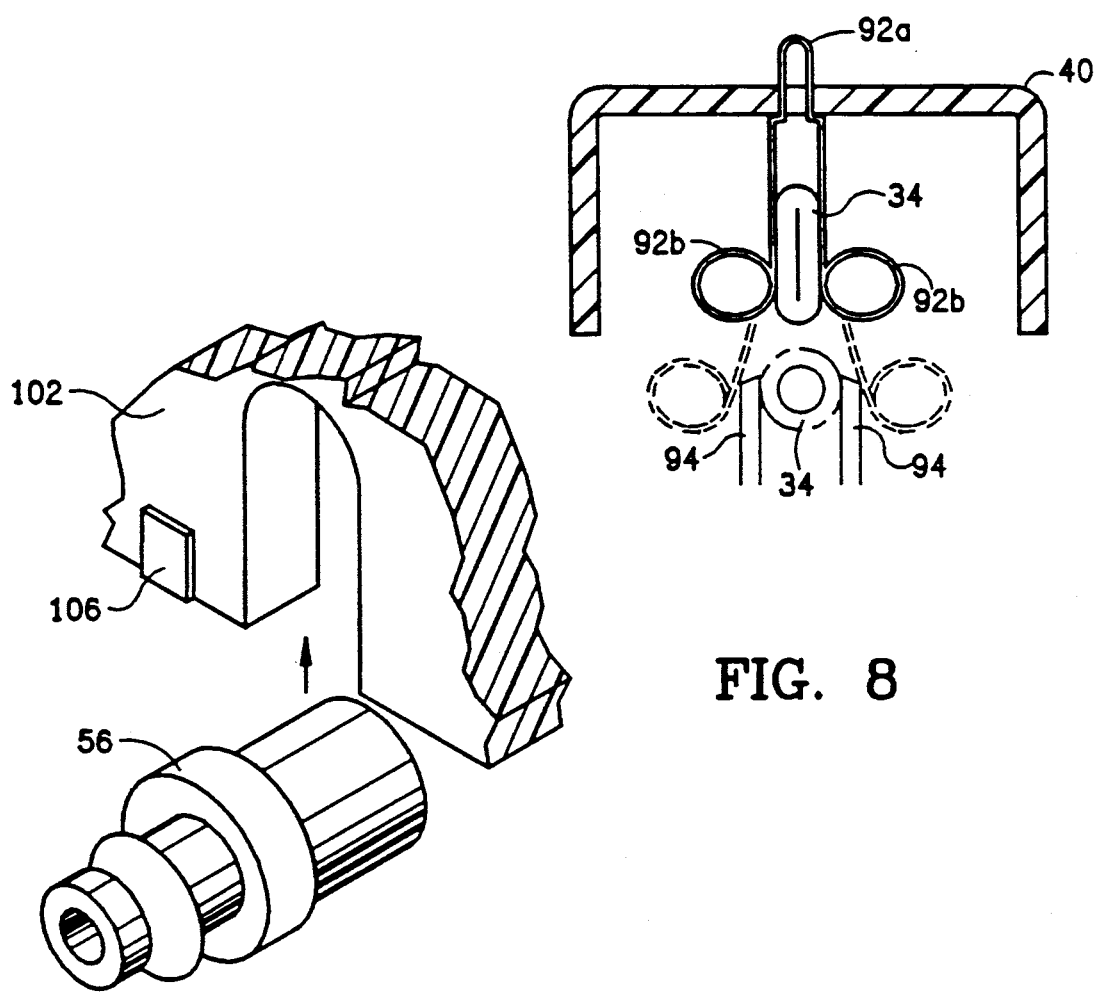
FIG. 8
FIG. 9

PROGRAMMABLE INFUSION SYSTEM

CROSS-REFERENCE TO RELATED APPLICATION

This application is related to co-pending U.S. patent application Ser. No. 07/518,777 entitled DISPOSABLE INFUSION APPARATUS AND PERISTALTIC PUMP FOR USE THEREWITH, filed on even date herewith.

BACKGROUND OF THE INVENTION

The present invention relates to medical devices, and more particularly, to an improved programmable infusion system for delivering intravenous drugs at a controlled rate to a patient.

It is often necessary to intravenously supply patients with pharmaceutically active liquids over a long period of time at a controlled rate. It is desirable that this be accomplished while the patient is in an ambulatory state.

The prior art includes devices that employ a bag filled with fluid medication that feeds by gravity through IV tubing having drip or other controllers. It is difficult for a patient to be ambulatory with a gravity fed infusion device. In addition, flow control in this type of device is very limited.

Another prior art infusion apparatus comprises an elastic bladder forming a liquid container, an elongated cylindrical housing enclosing the bladder, a flow control valve, and tubing for supply of the liquid to the patient. The elastic walls of the bladder expand along the walls of the cylindrical housing when filled with the liquid, and provide the pressure for expelling the liquid. The bladder is typically filled by hand with a syringe which often requires an inordinate amount of force. Another drawback is that the bladder is forced to expand into an unnatural elongated configuration along the housing walls as it is filled. As a result of this unnatural configuration, the pressure of the bladder varies widely with the volume of liquid therein. Therefore, in most cases this type of elastic infusion apparatus does not have a reasonably stable pressure and flow rate over the infusion period. Most of such devices either have a flow rate that decreases with pressure, which decreases with volume, or one that remains roughly constant until the end where it surges. Attempts have been made to control pressure and flow rates by means of complicated and expensive flow control valves and devices. Other approaches have utilized exotic and expensive elastic materials in an effort to control the pressures and flow rates.

Another type of infusion apparatus uses pressurized gas as the driving force for the intravenous liquid. In such systems there may be hydraulic feedback through the pneumatic source in order to precisely regulate hydraulic pressure. See for example U.S. Pat. Nos. 4,430,078 of Sprague, 4,335,835 of Beigler et al., and 4,327,724 of Birk et al. Such pneumatically driven infusion devices tend to have reducing flow rates and pressures as the stored pressurized gas source is exhausted.

Still another type of infusion apparatus employs a peristaltic or other positive displacement pump which is electrically driven. Programmable infusion pumps have been provided having the capability for precise tailoring of the fluid delivery rate parameters in different modes, such as, continuous, intermittent, PCA (patient controlled analgesic) and TPN (total parenteral nutrition). Originally such programmable infusion pumps were large and not well suited for ambulatory patients. They used complex and expensive replacement pump cartridges to maintain sterility. More recently, small programmable infusion pumps have been available with disposable plastic cartridges that engage a peristaltic pump. However such cartridges have been bulky and expensive and have required excessive drive power in the pumps, leading to rapid battery drain.

A major drawback of existing programmable infusion systems is that they require trained operators to program the same. There is an ever increasing desire in the health care field to get patients out of expensive hospital care environments and back to their homes. Many such patients require intravenously administered medications but are unable to program existing programmable infusion systems themselves and trained operators cannot economically visit their homes. In addition, many such patients are unable to change the delivery rates in accordance with subsequent physician prescriptions. Furthermore, they cannot effectively verify the prescribed delivery parameters.

Accordingly, it would be desirable to provide an improved programmable infusion system for delivering intravenous drugs at a controlled rate to an ambulatory patient that can be more easily programmed by a patient, and which will allow patient verification of the prescribed delivery parameters.

SUMMARY OF THE INVENTION

It is therefore the primary object of the present invention to provide an improved programmable infusion pump for an ambulatory patient which enables intravenous fluid delivery parameters to be readily programmed and verified by the patent.

Our invention comprises a programmable infusion system which includes a disposable IV tubing apparatus for conveying intravenous fluid from a source to a patient. The system further includes a compact, portable case having a receptacle for removably receiving a segment of the disposable apparatus. A peristaltic pump is mounted in the case for engaging the segment of the disposable apparatus and pumping intravenous fluid therethrough. A motor is mounted in the case and is connected for driving the pump upon energization thereof. A bar code reader is mounted in an edge portion of the case for sensing a bar code label attached to the source of intravenous fluid, such as a bag. The bar code label represents the prescribed fluid delivery parameters. These are read by the system when the edge portion of the case containing the bar code reader is passed over the bar code label. The bar code reader generates bar code signals representative of the fluid delivery parameters. A display is mounted in the case for visualizing information in alphanumeric form. A micro-controller mounted in the case receives the bar code signals and causes the display to provide a visual indication of the delivery rate parameters in alphanumeric form for verification by the patient. The micro-controller energizes the motor so that the peristaltic pump conveys the fluid through the disposable apparatus in accordance with the delivery rate parameters.

In the illustrated embodiment of our invention the system includes a keypad mounted in the case for enabling the user to send commands to the micro-controller. A detector mounted in the case optically detects the presence of a bubble inside the segment of the disposable apparatus and sends a bubble detect signal to the micro-controller. An occlusion detector mounted in the case detects an abnormal expansion of the segment of the disposable apparatus inside the case and sends an occlusion detect signal to the micro-controller.

In accordance with another aspect of our invention, a programmable infusion system is provided with the capability for communicating with a remote computer for receiving and conveying to the micro-controller commands for causing it to modify the delivery rate parameters. Thus the patient may communicate over a modem with a pharmacy or a nurse station so that a different infusion administration can be implemented.

The delivery rate parameters read in from the bar code label or communicated from the remote computer may include volume per unit time and total volume. They may also include various delivery modes selected such as continuous, Bolus, periodic and aperiodic.

The preferred embodiment of our programmable infusion system has the capability for detecting an interrupt condition such as the failure to load a disposable apparatus therein, an occlusion in the disposable apparatus, a motor failure, a pump failure, or a bubble in the disposable apparatus. The micro-controller can then de-energize the motor in response to the detection of an interrupt condition and cause the display means to display a warning of the interrupt condition in alphanumeric form. It can also cause an audible warning to be generated, such as a succession of beep tones, and a visible warning to be given in the form of an illuminated red LED. The system also preferably has the capability for detecting when the source of intravenous fluid is nearly empty and for activating the audible and/or visible warning in response thereto to advise the patient to replace the near empty bag of intravenous solution.

BRIEF DESCRIPTION OF THE DRAWINGS

FIG. 1 illustrates a preferred embodiment of our programmable infusion system. The case of the system which contains the pump and electronics is illustrated in phnatom lines. The disposable of our preferred embodiment is illustrated in relation to conventional IV tubing, IV bag, spike connector and leur fitting. The IV tubing segments are broken at various locations to make this figure compact.

FIG. 2 is an enlarged fragmentary view of the case of our invention illustrating a disposable installed therein and its relationship to the peristaltic pump of the system.

FIG. 3 is a further enlarged view of the perstaltic pump and the door of the disposable of our preferred embodiment. The IV tubing segments are not shown in this figure.

FIG. 4 is an enlarged view of the three segments of tubing that form part of the disposable of the preferred embodiment of our invention.

FIG. 5 is an enlarged side elevation view of one of the fingers of the perstaltic pump of the preferred embodiment showing how it squeezes shut the intermediate tubing segment of the disposable.

FIG. 6 is a side elevation view of one of the cam wheels of the perstaltic pump of our preferred embodiment. The motion of the cam wheel is illustrated in phantom lines.

FIGS. 7–9 illustrate details of the disposable door, tube clamp and IV tubing couplings.

DESCRIPTION OF THE PREFERRED EMBODIMENT

Figure 10:
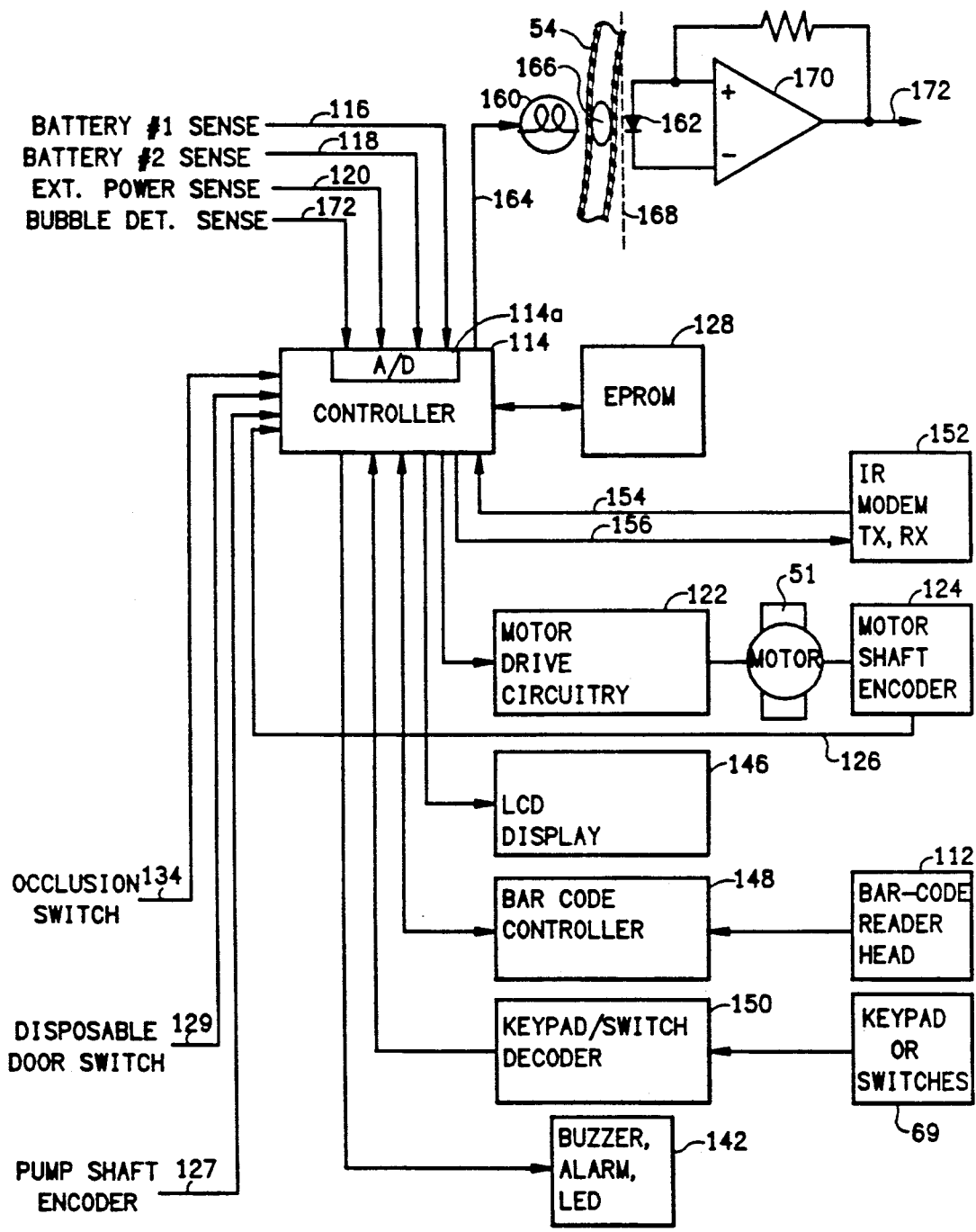
FIG. 10 is an overall functional block diagram of the electronics of our preferred embodiment.

Referring to FIG. 1, the illustrated embodiment 10 of our programmable infusion system includes a compact, portable rectangular case 12. By way of example, the case may be made of injection molded plastic and may measure approximately seven inches in length by approximately three and one-half inches in width (right side in FIG. 1) by approximately one inch in thickness (right side in FIG. 1).

A disposable IV tubing apparatus 14 (FIG. 2) may be releasably loaded or installed in a receptacle 16 (FIG. 2) in a long side edge of the case 12. The proximal end disposable IV tubing apparatus 14 is connected to a conventional spike 20 (FIG. 1). The patient inserts the spike into a conventional bag 22 of intravenous fluid in which the desired medications are dissolved. The distal end of the disposable IV tubing apparatus 14 is connected to a conventional male leur fitting 26 which in turn connects to a conventional IV catheter (not illustrated). A disposable IV fluid conveying means is a necessary requirement in an infusion system since it ensures sterility. It also prevents residual amounts of medication from one IV drug administration from being inadvertently delivered when a new IV drug administration commences.

Referring to FIG. 2, a peristaltic pump 30 is mounted inside the case 12 adjacent the receptacle 16. A pumping member 32 of the pump engages a linearly disposed intermediate segment 34 of the disposable IV tubing apparatus 14. The pumping member 32 comprises nine individual fingers 32a which slide back and forth toward and away from the intermediate IV tubing segment 34. The fingers 32a are moved by corresponding cam wheels 36 (FIG. 6). A flexible boot 33 (FIG. 2) surrounds the fingers and forms an interface between the fingers and the intermediate segment 34 of IV tubing. The peripheral edges of this boot are sealed to internal walls of the case to protect the pump from contamination. Each cam wheel 36 (FIG. 5) has a splined mounting hole 37 therethrough which is offset from the center of the wheel. Each finger 32a comprises a rectangular block having a circular hole in which a corresponding one of the cam wheels 36 rotates. The hole has a diameter slightly larger than the outside diameter of the wheel so that the wheel can rotate inside the hole and thereby pull the finger back and forth. The motion of one of the cam wheels is illustrated in phantom lines in FIG. 6.

The cam wheels 36 are mounted on a splined shaft 38 in progressive, offset alignment for individually reciprocating respective ones of the fingers 32a in a predetermined, timed sequence. The linearly disposed segment 34 of IV tubing is progressively squeezed by the fingers 32a so that intravenous fluid in the tubing is pumped therethrough.

The intermediate IV tubing segment 34 is preferably made of vinyl or silicone and has a maximum Durometer of seventy-five measured on the Shore A scale. By using a highly pliant, non-stiff resilient flexible tubing segment of this type, it is possible for the individual fingers 32a of the peristaltic pump 30 to each squeeze off and completely close the tubing segment during one cycle of its respective cam wheel. This squeezing off is illustrated in FIG. 6. This ensures a true positive displacement pump in which a single rotation of the splined shaft 38 will cause a predetermined volume of fluid to be pumped through the disposable IV tubing apparatus 14. Having such a non-stiff disposable IV tubing apparatus 14 also ensures that less torque is required to rotate the splined shaft 38, thereby resulting in an overall reduction in energy consumption when the peristaltic pump is electrically driven from battery power as hereafter described.

The fingers 32a preferably have small teats 32b (FIG. 6) projecting from the ends thereof. These teats engage and squeeze the intermediate IV tubing segment 34. It has been determined that these teats ensure that the tubing segment 34 will be completely squeezed off during each cycle of each finger. It is important to understand that the intermediate tubing segment 34 must have a minimum amount of stiffness and resilience or else it will not open and close in a manner that will permit it to function as a peristaltic pump. Preferably the tubing segment 34 has a minimum Durometer of thirty-five measured on the Shore A scale.

Referring again to FIG. 2, the programmable infusion system 10 includes means for releasably mounting the intermediate IV tubing segment 34 adjacent the pumping member 32. The intermediate tubing segment 34 is mounted to a door 40 having a hook-shaped member 40a (FIG. 3) at one end and a compressible clasp 40b at the other end. The hook-shaped member 40a of the door may be engaged by the patient with a shoulder 16a (FIG. 2) located at one end of the receptacle 16 in the case 12. The other end of the door is then swung in and the clasp 40b snaps into the other end of the receptacle 16. The intermediate IV tubing segment 34 is squeezed between the individual fingers 32a and a compressible, resilient pad 42 (FIGS. 3 and 6) supported by the innerside of the door 40. This pad may be made of polyurethane foam.

The shaft 38 (FIG. 3) which supports the cam wheels 36 is journaled at opposite ends in ball bearings 44. A gear 46 rigidly mounted on one end of the shaft 38 meshes with another gear 48 (FIG. 2) rigidly mounted on another shaft 50 of a DC motor module 51 having an internal 141:1 gear reduction. In other words, one-hundred and forty-one rotations of the armature of the DC motor turns the shaft 50 one revolution and thus the cam shaft 38 one revolution.

Referring to FIG. 4, the disposable IV tubing apparatus 14 has a proximal tubing segment 52 and a distal tubing segment 54 connected to opposite ends of the intermediate IV tubing segment 34 by means of couplings 56 and 58. These couplings are attached to the underside of the door 40 as hereafter described in conjunction with FIG. 9.

Figure 11:
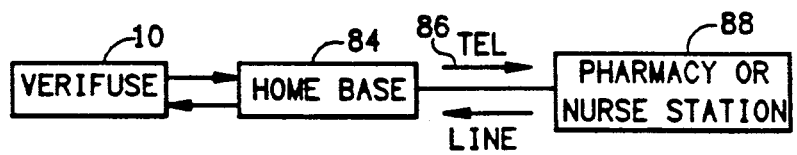
FIG. 11 is a functional block diagram illustrating the modem communication of the preferred embodiment of our system with a remote pharmacy or nurse station.

Referring again to FIG. 1, a liquid crystal display 146 is mounted in the case 12. A bar code reader head 110 (FIG. 2) is mounted in the edge of the case 12 opposite the disposable receptacle 16 so that a patient holding the case can scan the bar code label 112 (FIG. 1) on the IV bag 22. Four independently actuable push-buttons 70, 72, 74 and 76 (FIG. 1) are positioned on the front face of the case 12. Together these push-buttons form a four-button keypad which enables the patient to send commands to a micro-controller in the system as hereafter described in great detail. The LCD display 146 is preferably a sixteen character by two line, super twist liquid crystal display. One end of the case 12 (right side in FIG. 2) is provided with a male electrical connector 78 for establishing electrical connection with an external DC power supply (not illustrated). An infrared transmitter 80 and an infrared receiver 82 are also mounted at this end of the case 12 so that the case can be inserted into a home base unit shown diagrammatically at 84 in FIG. 11. The home base unit 84 contains a modem for establishing communication over telephone lines 86 with a personal or other computer also equipped with a modem at a pharmacy or nurse station 88. The home base unit 84 is physically configured to provide a receptacle in which the lower end of the case 12 may be positioned. The home base unit also has a infrared transmitter and a infrared receiver which are physically located adjacent the infrared receiver and infrared transmitter, respectively, of the system 10 when the system is plugged into the home base unit. Once a communication link has been established with the computer at the pharmacy or nurse station 88, the modem will provide infrared T×D and R×D signals to the micro-controller of the system 10 to allow re-programming of the fluid delivery control rate instructions. The transmission and reception of data from the system via the infrared transmitter and detector 80 and 82 may be accomplished through a conventional RS-232 data link.

Referring to FIG. 4, the intermediate IV tubing segment 34 preferably has an inside diameter of approximately 0.125 inches. Silicone and VINYL tubing can be commercially obtained having the desired stiffness. The proximal segment 52 and the distal segment 54 are each preferably made of clear polyvinyl chloride (PVC) having an outside diameter of approximately 0.140 inches and an inside diameter of approximately 0.088 inches. This clear PVC tubing is larger in both inside and outside diameter than the conventional PVC tubing segments 55a and 55b (FIG. 1) which connect the segments 52 and 54 to the spike 20 and male lure fitting 26, respectively.

In an actual prototype of our preferred embodiment, the designed maximum delivery rate is approximately three hundred milliliters per hour. The minimum designed delivery rate is approximately 0.1 milliliters per hour. The delivery resolution is approximately 0.1 milliliters per hour for 0.01 through 99.9 milliliters per hour and approximately one milliliter per hour for approximately one hundred to three hundred milliliters per hour. In the prototype, the designed maximum volume to be infused (VTBI) is one thousand milliliters and the minimum volume to be infused (VTBI) is approximately 0.1 milliliters. The designed "keep vein open" (KVO) rate is approximately one milliliter per hour for one through three hundred milliliter per hour rates and approximately 0.1 through 0.99 milliliters per hour for 0.1 through 0.99 milliliter per hour rates.

Referring to FIG. 7, the door 40 has a rectangular aperture 90 formed adjacent the hook-shaped member 40a. A resilient metal tubing squeezer 92 has an upper end 92a which is tightly received in the aperture 90 in the door 40. The squeezer 92 has a pair of parallel downwardly extending arms which terminate in coiled sections 92b. Referring to FIG. 8, when the disposable is assembled, the intermediate segment 34 is squeezed shut between the coiled sections 92b. When the door 40 is installed into the receptacle 16 of the case 12, the hook-shaped member 40a is engaged with the shoulder 16a (FIG. 2). The other end of the door having the clasp 40b is then swung toward the case. As this happens, the coiled sections 92b of the tubing squeezer 92 engage upstanding projections 94 (FIG. 8) in the receptacle. These projections are spaced so that the coiled sections are displaced outwardly away from the intermediate tubing segment 34 thereby unclamping the same. This is illustrated in phantom lines in FIG. 8. The squeezer performs a very important function. Namely, if the disposable IV tubing apparatus 14 should be inadvertently removed from the case 12 it will squeeze off the intermediate tubing section 34 and prevent freeflow of intravenous fluid by gravity action.

Referring to FIG. 3, the clasp 40b consists of a V-shaped element. The door 40 is preferably made of injection molded plastic and the V-shaped clasp 40b is compressible upon swinging the clasp into the receptacle 16 in the case. This allows a wedge-shaped projection 96 on the clasp 40b to clear and snap into engagement behind an L-shaped latch 98.

Further details of the disposable IV tubing apparatus 14 are visible in FIG. 9. The coupling 56 is received in a slot in a bracket 102 which extends from the underside of the exterior wall of the door 40 near the clasp 40b. The coupling 56 is solvent, welded or bonded to the bracket 102. The coupling 58 is similarly received in another recess formed in the hook-shaped member 40a. Again the coupling 58 is solvent bonded to the member 40a. A magnet 106 (FIG. 9) is attached to the bracket 102 and detected by a Hall effect switch 108 (FIG. 3) adjacent the receptacle 16. The Hall effect switch is connected to the micro-controller hereafter described so that the output thereof will indicate whether or not a disposable has been correctly loaded into the case 12.

Referring again to FIG. 2, the bar code reader head 110 is capable of sensing the bar code label 112 (FIG. 1) attached to the bag 22 of intravenous fluid. The bar code label 112 represents encoded information regarding the prescribed fluid delivery parameters. These are read by the system when the edge portion of the case 12 containing the bar code reader head 110 is swiped or passed over the bar code label 112. The bar code reader 112 is connected to a bar code controller circuit 148 (FIG. 10) which generates bar code signals representative of the fluid delivery parameters. One suitable commercially available bar code reader is the Welch Allyn 022 088 (TBD#) three of nine code compatible.

FIG. 10 is a functional block diagram of the electronics of the preferred embodiment 10 of our system. It includes a micro-controller 114. One suitable micro-controller is MOTOROLA 68HC11F1-FN which has a built-in A/D interface 114a. DC battery power may be supplied to the micro-controller 114 through inputs 116 and 118. DC power from an external power supply may be supplied via line 120 which is connected to male electrical connector 78 (FIG. 2) mounted at one end of the case 12. The motor module 51 which drives the peristaltic pump 30 is itself driven by motor drive circuitry 122 (FIG. 10) which is controlled by the micro-controller 114. A motor shaft encoder 124 is associated with the shaft of the motor in the module 51 and provides signals to the micro-controller on line 126.

Operating instructions in the form of a computer program for carrying out all of the logical operations of the system are stored in a peripheral memory connected to the micro-controller. In the preferred embodiment, this memory takes the form of an erasable programmable read only memory (EPROM) 128 (FIG. 10). The micro-controller also receives signals on line 127 from a pump shaft encoder. The signals on lines 126 and 127 are used by the micro-controller in delivering a predetermined volume of intravenous fluid at a predetermined rate.

The Hall effect switch 108 is connected to the micro-controller via line 129 so that the micro-controller can tell if a disposable apparatus 14 has been correctly loaded. An occlusion detect switch 130 (FIG. 3) is mounted to the bottom wall 132 of the receptacle 16 in the case. This switch is connected via line 134 (FIG. 10) to the micro-controller 114. Returning again to FIG. 3, the occlusion switch 130 has a vertically reciprocable actuating pad 136 which is depressed and actuated when there is a blockage in the disposable 114 causing the intermediate segment 34 to expand abnormally. This detection of an occlusion is sensed by the micro-controller which de-energizes the peristaltic pump to prevent further pumping until the condition has been detected. The micro-controller also sends visual and audible warnings to the patient as hereafter described in greater detail. The occlusion switch 130 is mounted on a bracket 138, the position of which is vertically adjustable by turning screw 140 to thereby adjust the sensitivity of the occlusion detection.

An audible (buzzer) and LED alarm are indicated diagrammatically at 142 in FIG. 10. The alarm 142 may include a red LED 144 (FIG. 2) mounted at one end of the case 12. The LCD display 146 is also mounted at the same end of the case 12 for visualizing the fluid delivery parameters in alphanumeric form.

One suitable commercially available display is a sixteen character by two line, super twist liquid crystal display, with no back light, available from NEC, of Japan. The display 146 provides a visual verification to the patient of the delivery parameters which have been entered either by reading a bar code label or by modem connection with a remote computer at the pharmacy or nurse station. The display 146 also provides a visual indication of the operation of the system while pumping. It further provides a visual indication of any operational faults or failures as hereinafter described in greater detail.

Referring again to FIG. 10, the bar code reader head 112 is connected to the bar code micro-controller 148 which is in turn connected to the micro-controller 114. One suitable commercially available bar code micro-controller is the Welch Allyn LTS 3 C-CMOS decoder 3 of 9 compatible. The DC power supplied on lines 116 and 118 may be provided by a pair of nine-volt lithium or alkaline batteries. The motor encoder 124 may provide sixteen pulses per revolution. One suitable commercially available motor module having a built-in gear reduction and encoder is sold under the trademark MICRO-MO. The pump shaft encoder which provides the signals to the micro-controller on line 127 may be provided by a simple Hall effect switch which provides one pulse per revolution of the shaft.

The push button switches 70, 72, 74 and 76 which together comprise a keypad 69 (FIG. 10), are connected to a conventional keypad/switch decoder 150 which in turn is connected to the micro-controller 114. The infrared transmitter and receiver 80 and 82 and the modem are illustrated collectively as box 152 in FIG. 10. They are connected to the micro-controller 114 via lines 154 and 156.

Our system further includes a bubble detector module which detects the presence of a bubble in the clear PVC tubing segment 54. As shown in FIG. 2, a bubble detector module 158 is physically positioned inside the case 12 along the side edge thereof, aft of the door 40. The module 158 includes a lamp 160 (FIG. 10) which is positioned on one side of the distal IV tubing segment 54. The module 158 further includes a germanium detector 162 which is positioned on the other side of the distal tubing segment 54. The lamp 160 may comprise an infrared type lamp or a light emitting diode. However, preferably the lamp 160 is an incandescent lamp which is energized by the micro-controller 114 via line 164. The lamp 160 may be pulsed or it may be illuminated under a steady DC current. Most intravenous fluids are largely made up of water. Intravenous fluids which are not made up of water are generally always opaque and therefore it is easy to detect the existence of a bubble such as 166 in the clear distal tubing segment 54. Our bubble detection scheme takes advantage of the fact that water has a peak absorption region between about 1400-1500 nanometers. The bubble detect module 158 further includes a filter 168 positioned between the clear IV tubing segment 54 and the lamp 160. This filter has a band pass limited to the foregoing absorption region of water. Thus, when bubble 166 arrives between lamp 160 and detector 162, the germanium detector 162 is illuminated with radiation in the band pass region. This detector is connected to a transimpedance amplifier 170 which sends a bubble detect signal to the micro-controller on line 172.

Having described the hardware of the preferred embodiment of our programmable infusion system 10, its operation can now be described in further detail. This system is capable of providing, a selectable delivery mode. One such mode is a continuous rate/volume mode in which fluid is delivered at a fixed rate for a fixed volume during a single administration. Another mode allows a so-called Bolus type delivery similar to PCA. The patient initiates delivery at the desired time with a fixed volume, and not-to-exceed limits on dosage (milliliters/per hour) within a total time period. Another mode allows periodic delivery. On periodic time boundaries, (for example 3, 6, 9 . . . hours) the system delivers specific VTBI at programmed rates for N iterations, including KVO. Another mode enables aperiodic delivery. In this mode, the system is programmed to deliver a specific VTBI at a specified rate for a specified time. This can be done in any arbitrary sequence for a fixed number of unequal time intervals. This could include ramping up and down, as in TPN. The peristaltic pump of the system delivers fluid with flow rates and total volume accuracy of plus or minus 5%, for any prescribed delivery mode. Accuracy is measured continuously at delivery rates greater than 3-5 milliliters per hour, and over a specified time period for rates less than 3-5 milliliters per hour (TBD).

The system may be programmed by passing the bar code reader head 110 over a bar code label 112. By way of example, the bar code label may encode information in HBIC format (3 of 9) describing both the type of medication or product and 3 of 9 for the desired delivery mode. Upon reading a bar code label, the micro-controller immediately displays the foregoing information in alphanumeric form on LCD display 146 to allow the patient to verify this information. Patient can signify his or her verification of this information by actuating the push button 72 (FIG. 1) on the face of the case. The micro-controller can be programmed not to proceed with the administration unless the patient has indicated his or her acknowledgement of this verification. The bar code reader provides an easy and convenient way for an unskilled patient to program the system for continuous, periodic or aperiodic delivery with given rates, VTBI or times.

The disposable IV tubing apparatus 14 must be installed in the receptacle in the side of the case 12 in order for the system to be programmed. In addition the system must be reprogrammed if the disposable has been removed. This is a safety precaution. The EPROM 128 stores tables of VTBI, rate and delivered volume of values. The four push buttons 70, 72, 74 and 76 (FIG. 1) can be used to actuate the following four functions. The first push button 70 actuates a stop/start function under which any pumping cycle of the system can be started or stopped by successive actuation of the corresponding push button. The second push button 72 actuates a verify function which is used when checking and verifying programming information read in through the bar code reader. The third push button 74 actuates a prime function which, by actuation of a corresponding push button, causes the micro-controller to fill a brand new disposable which has just been loaded into the system with fluid from the intravenous fluid source. The fourth push button 76 actuates a Bolus function which provides small predetermined delivery of fluid upon user demand.

A green LED 172 (FIG. 2) at one end of the case flashes at a regular rate when the system is ON and functionally normal. The red LED 144 at the same end the case is illuminated when there is a system failure, either electronic or mechanical. As previously indicated, the illumination of the red LED is preferably also accompanied by an audible alarm. Such failures can include the detection of a bubble in the disposable, the detection of an occlusion in the disposable, the failure to load a disposable into the system, a motor failure or a pump failure.

The micro-controller 114 has the capability for detecting an interrupt condition such as the failure to load a disposable apparatus, an occlusion being detected, a motor failure, a pump failure or a bubble in the disposable apparatus. The micro-controller can then de-energize the motor in response to the detection of an interrupt condition and cause the display means to display a warning of the interrupt condition in alphanumeric form. It can also cause an audible warning to be generated, such as a succession of beep tones, and a visible warning to be given in the form of illumination of the red LED 144.

The micro-controller 114 can also monitor, detect, shut down and provide a warning of other circuit failures and conditions. These would include low battery condition, i.e. 7.5 volts (TBD), very low battery condition, i.e. 6.5 volts (TBD), and use of the power supply with a battery in place. It is important to configure the power supply such that if alkaline batteries are in place in the unit, they will not be charged by the power supply since such batteries can explode.

The micro-controller 114 preferably has internal watch dogs. It should be able to detect, provide a warning, and shut down the system upon detection of a failure in any watch dog or failure of the internal counter of the micro-processor. A motor failure is indicated by the motor turning when not pulsed, or not turning when pulsed, and can be detected by the motor encoder. Pump failure can be due to failure in the gear reduction or peristaltic pump mechanism. Such a condition would be detected by the motor turning without the peristaltic encoder turning.

Preferably the system is also capable of detecting when an infusion is nearly complete, i.e. when a bag of intravenous fluid is nearly empty. This can be detected by the system being programmed ahead of time with the total volume of intravenous fluid to be dispensed and by calculating the volume, periodically, of fluid that has been dispensed. The VTBI nearly infused (bag empty) can result in the micro-processor causing the audible tone generator to beep every five seconds, and cause the red LED 144 to be illuminated.

All of the foregoing interrupts/failures/conditions are also simultaneously accompanied by an alphanumeric warning on the LCD display 146. Preferably the micro-controller is provided with a non-volatile random access memory (RAM) in case of power down or power failure so that an interrupt, failure or other fault condition can be displayed when power is restored. This non-volatile RAM may be part of a micro-processor or may be a separate peripheral memory chip connected to a micro-processor. It should provide at least three hundred bytes to permit the storage of at least one hundred per pump protocol instructions.

The peristaltic pump 30 is a single channel, linear peristaltic pump having nine reciprocating fingers 32a. The intermediate IV tubing segment 34 is highly flexible as previously indicated. In a preferred embodiment of the disposable 14, the intermediate IV tubing segment 34 is made of silicone and has an inside diameter of approximately 0.125 inches. Approximately 0.12 milliliters of intravenous fluid are pumped through the intermediate IV tubing segment 34 for each single revolution of pump shaft 38. The combined motor and gear reduction module 51 also preferably includes a built-in motor encoder. One suitable unit is the MICRO-MO Model 1624006S. It uses TEFLON (Trademark) fixotropic lubricant. A conventional Robert's clamp 23 (FIG. 1) may be provided on the segment of conventional IV tubing 55b for closing off the same.

Figure 12A:
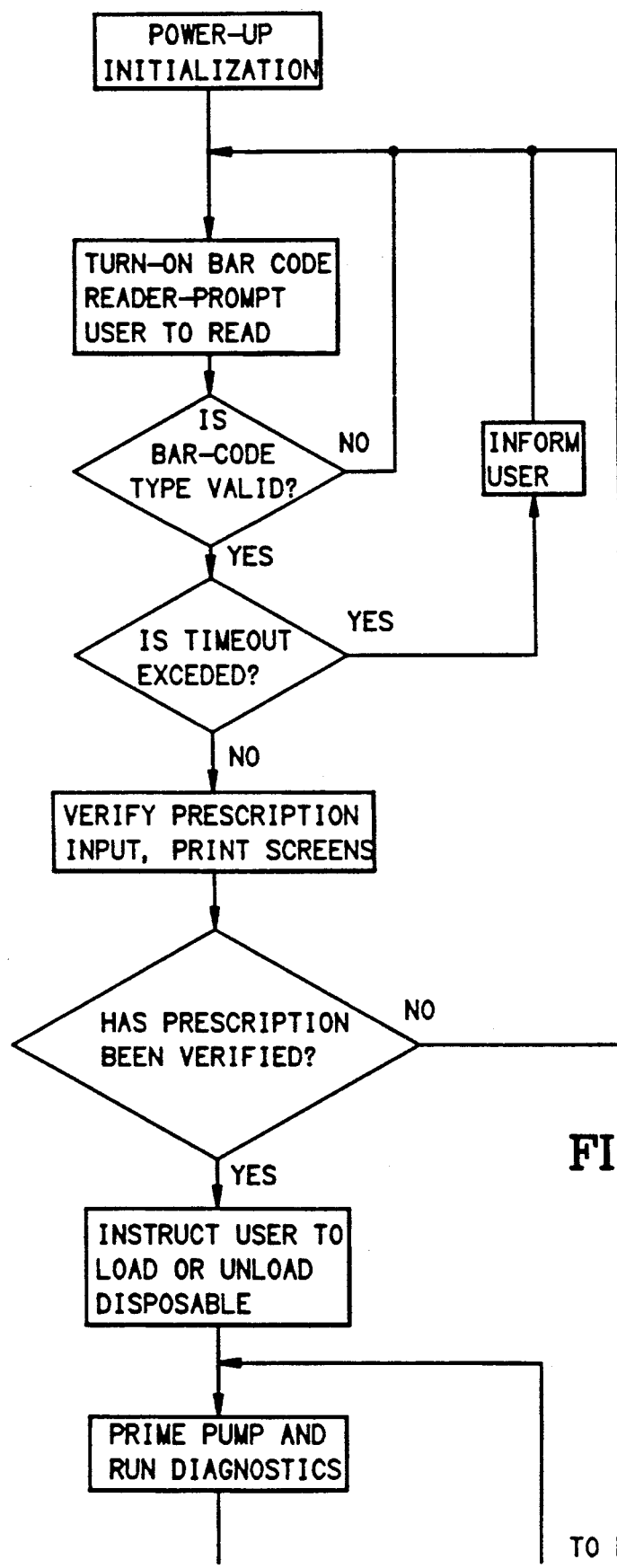
FIGS. 12A and 12B taken together comprise a flow diagram illustrating a logical operation of the preferred embodiment of our infusion system.
Figure 12B:
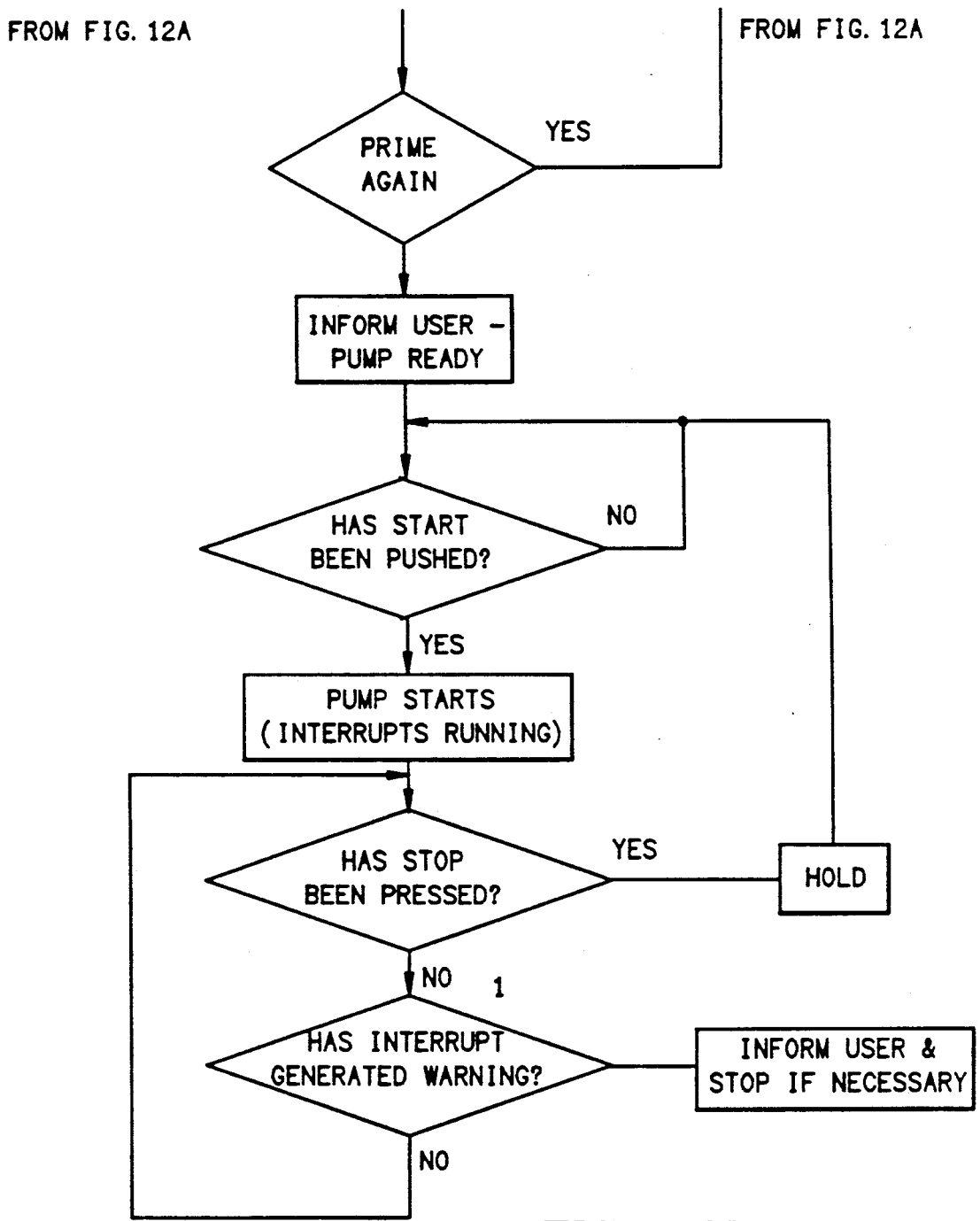

Further details of the operation of the preferred embodiment of our system will be understood by way of reference to the flow diagram of FIGS. 12A and 12B. First of all, when the system is powered ON, the green LED 172 is illuminated. The power may be turned ON by plugging in batteries, or connecting the external power supply. The system then performs an initial check within three seconds. The LCD display fills with asterisks in all sixteen by two locations. The audible alarm sounds and the red LED 144 is illuminated. The LCD can then display the name of the currently loaded infusion pump operation program such as—BLOCK MEDIAL VERSION 2.0—.

Next the micro-controller causes the LCD to display the following message—SYSTEM READY-SCAN BAR CODE—. The system waits for the operator to scan a bar code label, and provides an audible beep sound when a legitimate bar code label has been read. The LCD then displays the following message—BAR CODE-READ VERIFY—. This prompts the patient to actuate push button 72 to verify the programmed medication type and delivery parameters. The LCD may then display, for example, the following message—CONTINUOUS MODE-VERIFY—. The user is then prompted to actuate the verify push button 72 a second time. The micro-controller then causes the LCD to display the delivery rate parameters in a message such as—300 ML/HR-VERIFY—. The patient is then again prompted to actuate the verify push button 72 and the LCD displays, in this example, the following message—VTBI EQUALS 600 ML-VERIFY—. The patient is again prompted to actuate the verify button 72 at which time the micro-controller causes the LCD to display the following message—PROTOCOL VERIFIED LOAD SET & PRIME—. The patient then actuates the prime push button 74 which causes the micro-controller to actuate the peristaltic pump 30 to draw intravenous fluid from the IV bag 22 all the way through to the male leur fitting 26. The patient then either connects a catheter and inserts it into his or her body, or connects the male leur fitting to a catheter already surgically in place. Once this is accomplished, the user again actuates push button 70 causing the unit to start and display the following message—SYSTEM READY TO BEGIN—. Thereafter, intravenous fluid will be pumped by the system into the patient in accordance with the programmed delivery parameters. During this administration the micro-controller energizes the pump motor to accomplish the described delivery rate and calculates the volume of fluid delivered via signals from the pump shaft encoder and the motor shaft encoder. The data stored in both the EPROM and RAM memories is used to administer the intravenous fluid in the prescribed manner.

If a periodic delivery mode has been programmed from the bar code label, the LCD may display the following sequence of messages with the patient actuating the verify push button 72 in each instance: 1)—PERIODIC MODE-VERIFY—; 2)—TWO HUNDRED ML EVERY XX HOURS-VERIFY—; 3)—RATE EQUALS THREE HUNDRED ML/HR-VERIFY—; 4)—TOTAL TIME EQUAL FOUR HOURS-VERIFY—; and 5)—PROTOCOL-VERIFY XX—.

If the aperiodic mode has been programmed from the bar code label, the LCD may cause the following displays to appear: 1)—APERIODIC MODE-VERIFY—; 2)—ONE THREE HUNDRED ML/HR, FIFTY ML XXMIN-VERIFY—; and 3)—TWO FIFTY ML/HR, 25 ML XX MIN-VERIFY—.

If at any time the patient observes a visual display of the intravenous fluid type and/or delivery parameters that he or she feels is incorrect, the patient can delay the intravenous administration and phone his or her physician, pharmacist or nurse for instructions. This may result in the patient loading the case 12 into the home base 84 (FIG. 11) for modem communication with the pharmacy or nurse station 88. The system could then be directly programmed by the physician or nurse through his or her personal computer. If at any time a system fault is detected which can not be corrected by the patient, i.e. power supply failure, motor failure, etc., intravenous administration can be delayed and the appropriate assistance obtained. This may require that a replacement system be provided so that repair work can be accomplished on the system which has failed.

The bar code labels containing the fluid rate delivery programming can be readily generated by a pharmacist. This may be accomplished through a personal computer connected to a laser printer capable of printing the bar code information on peel-off adhesive labels. Each pharmacist can be provided with a computer program on floppy disk, tape or other suitable media. The program will enable the pharmacist to enter conventional delivery parameters which have been prescribed by the physician into the computer by keyboard which will in turn convert the information into a suitable bar code label. Upon printing in the laser printer, this bar code label can be peeled off and adhesively applied to the bag containing the appropriate dosage of intravenous fluid medication.

While we have described a preferred embodiment of our improved programmable infusion system, it should be understood that modifications and adaptations thereof will occur to persons skilled in the art. Therefore, the protection afforded our invention should only be limited in accordance with the scope of the following claims.

We claim:

1. A programmable infusion system, comprising:
   disposable IV tubing means for conveying intravenous fluid from an IV fluid bag to a patient;
   a compact, portable case having a receptacle for removably receiving an intermediate pliant segment of the disposable IV tubing means;
   peristaltic pump means mounted in the case for engaging the intermediate pliant segment of the disposable IV tubing means and pumping intravenous fluid therethrough;
   motor means mounted in the case for driving the peristaltic pump means upon energization thereof;
   bar code reader means mounted in an edge portion of the case for sensing a bar code label associated with the IV fluid bag representing a plurality of fluid delivery parameters when the edge portion of the case is passed over the label and for generating bar code signals representative thereof;
   display means mounted in the case for visualizing information in alphanumeric form; and
   control means mounted in the case for receiving the bar code signals and causing the display means to display the delivery rate parameters in alphanumeric form for verification by the patient and for energizing the motor means so that the peristaltic pump means will pump the intravenous fluid through the intermediate segment of the disposable IV tubing means in accordance with the delivery rate parameters.

2. A programmable infusion system according to claim 1 and further comprising keypad means mounted in the case for enabling a user to send commands to the control means.

3. A programmable infusion system according to claim 1 and further comprising means positioned inside the case adjacent the receptacle for detecting a bubble inside the disposable IV tubing means and for sending a bubble detect signal to the control means.

4. A programmable infusion system according to claim 1 and further comprising means mounted to a bottom wall of the receptacle for detecting an expansion of the segment of the disposable IV tubing means indicating the existence of an occlusion and for sending an occlusion detect signal to the control means.

5. A programmable infusion system according to claim 1 and further comprising means for communicating with a remote computer for receiving and conveying to the control means commands for causing the control means to modify the delivery rate parameters.

6. A programmable infusion system according to claim 1 wherein the delivery rate parameters include volume per unit time and total volume.

7. A programmable infusion system according to claim 1 wherein the delivery rate parameters include a delivery mode selected from the group consisting of continuous, Bolus, periodic and aperiodic.

8. A programmable infusion system according to claim 1 and further comprising means mounted in the case for generating an audible warning signal, and further wherein the control means includes means for detecting when the source of intravenous fluid is nearly empty and for activating the audible warning means in response thereto.

* * * * *